United States Patent
Sarvazyan et al.

(10) Patent No.: US 7,307,730 B2
(45) Date of Patent: *Dec. 11, 2007

(54) APPARATUS AND METHOD FOR MEASURING TEMPERATURE DEPENDENT PROPERTIES OF LIQUID

(75) Inventors: Armen P. Sarvazyan, Lambertville, NJ (US); George Eric Plum, Columbus, OH (US); Sergey Tsyuryupa, Levittown, PA (US)

(73) Assignee: IBET, Inc., Columbus, OH (US)

( * ) Notice: Subject to any disclaimer, the term of this patent is extended or adjusted under 35 U.S.C. 154(b) by 72 days.

This patent is subject to a terminal disclaimer.

(21) Appl. No.: 11/456,328

(22) Filed: Jul. 10, 2006

(65) Prior Publication Data

US 2006/0238763 A1    Oct. 26, 2006

Related U.S. Application Data

(63) Continuation-in-part of application No. 10/986,272, filed on Nov. 12, 2004, now Pat. No. 7,075,652.

(51) Int. Cl.
G01N 21/00 (2006.01)
G01N 21/64 (2006.01)

(52) U.S. Cl. .................. 356/432; 356/244; 356/246; 250/458.1

(58) Field of Classification Search ........ 356/432–444, 356/244, 246, 319, 408–410; 250/574–575, 250/458.1, 461.1 R; 364/160, 148
See application file for complete search history.

(56) References Cited

U.S. PATENT DOCUMENTS 4,180,739 A * 12/1979 Abu-Shumays .......... 250/461.1
4,523,097 A * 6/1985 Allington ................. 250/458.1
4,566,807 A * 1/1986 Koolen ....................... 374/112
4,626,205 A * 12/1986 Barkley et al. ............. 432/225
4,676,639 A * 6/1987 Van Wagenen ............. 356/246
4,739,467 A * 4/1988 Furusawa .................... 700/28
5,140,169 A * 8/1992 Evens et al. ................ 250/576
5,173,742 A * 12/1992 Young ........................ 356/319
5,183,042 A * 2/1993 Harjunmaa et al. ......... 600/309
6,058,774 A * 5/2000 Rengshausen ........... 73/204.24
6,618,144 B1 * 9/2003 Reed .......................... 356/343
6,678,052 B1 * 1/2004 Hanagandi et al. ......... 356/440
6,717,665 B2 * 4/2004 Wagner et al. ............. 356/244

* cited by examiner

Primary Examiner—Sang H. Nguyen
(74) Attorney, Agent, or Firm—Boris Leschinsky

(57) ABSTRACT

The present invention relates generally to an improved method and apparatus for measurement of properties of a sample as a function of temperature. The method and apparatus are based on formation of a stable temperature gradient through the holding fixture such as a cell or a plate containing the sample under study, measurement of the property of interest as a function of position, and relating the positions of the measurements to the temperature of the studied sample at that position. In the preferred application, thermal and thermodynamic properties of solutes are obtained. Provisions are described to combine optical interrogation with Raman spectroscopy. Alternate technique of interrogation is total internal fluorescence reflection. Chemical reaction rates as function of temperature can be advantageously studied including reactions catalyzed by enzymes.

20 Claims, 10 Drawing Sheets

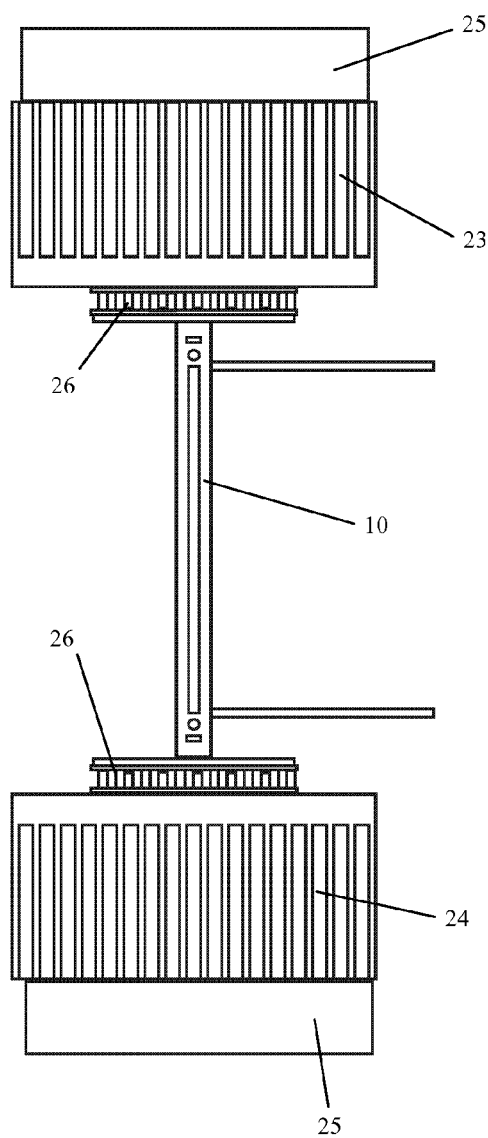
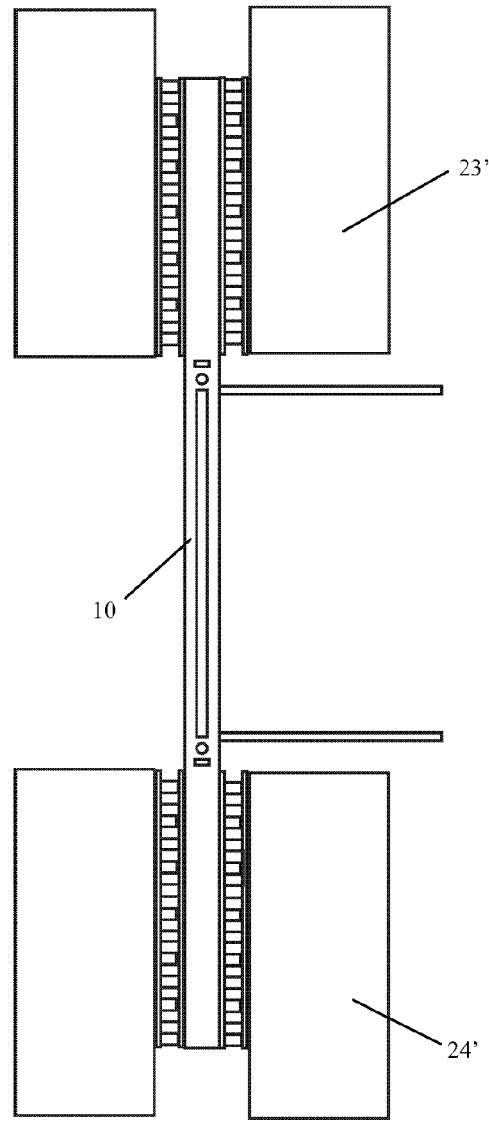
Figure 6                    Figure 7

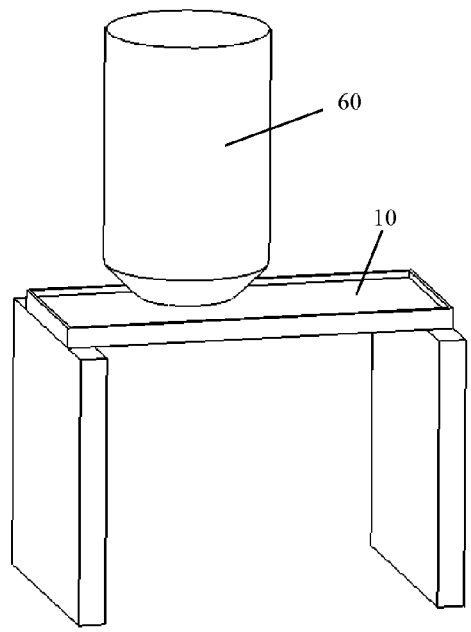
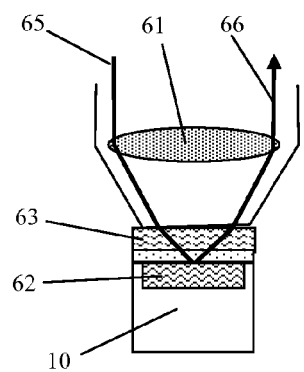
Figure 8 C
Figure 8 D
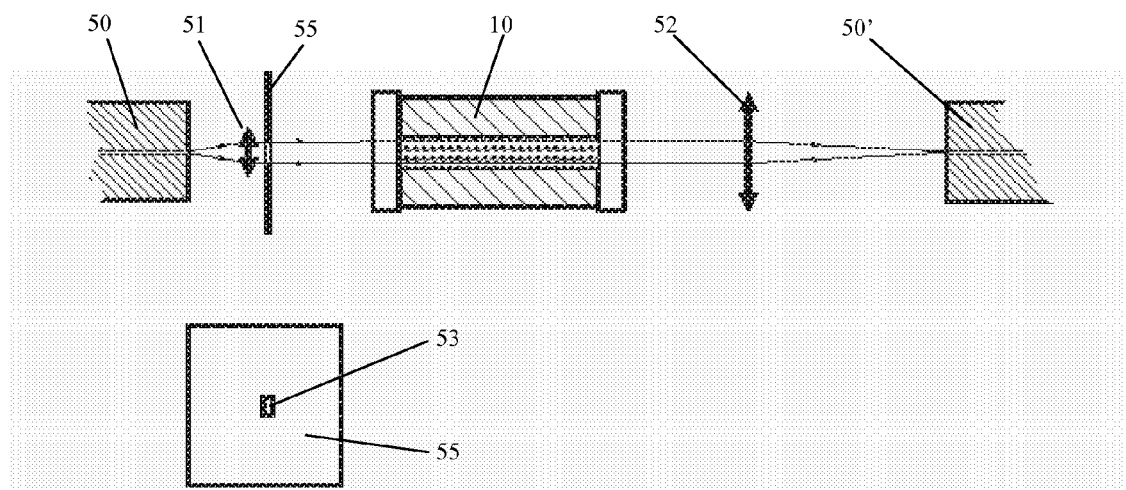
Figure 9

APPARATUS AND METHOD FOR MEASURING TEMPERATURE DEPENDENT PROPERTIES OF LIQUID

CROSS-REFERENCE DATA

This is a continuation-in-part of U.S. patent application Ser. No. 10/986,272 filed Nov. 12, 2004, now U.S. Pat. No. 7,075,652 entitled "An Apparatus and Method for Measuring Temperature Dependent Properties of Liquid", which is incorporated herein by reference in its entirety.

STATEMENT REGARDING FEDERALLY SPONSORED RESEARCH OR DEVELOPMENT

This invention was made with Government Support under GM62692 awarded by the PHS. The Government has certain rights in the invention.

BACKGROUND OF THE INVENTION

The present invention relates generally to measuring temperature dependent properties of liquids or solid samples contained within a liquid bath or otherwise thermally coupled to the holding fixture. More particularly, the apparatus and methods of the invention describe an apparatus including a liquid containing fixture with a predetermined temperature gradient thereacross equipped with an optical means to measure temperature-dependent optical properties of the liquid of interest contained therein.

Calorimetry is a well-known method of evaluating the thermal and thermodynamic properties of liquids. Prior art in calorimetry is well described in numerous textbooks on physics and physical chemistry and in monographs devoted to the subject. When the liquids display favorable optical properties, methods for indirect determination of thermal and thermodynamic properties are known. Several formulations based on the van't Hoff equation for example have been described in the art aiming at extracting thermodynamic information for non-calorimetric observables measured as a function of temperature. The words "observable" and "property" are used interchangeably in this description and have the same meaning. These van't Hoff methods can be advantageously applied to temperature-dependent spectroscopic data.

Liquids present a variety of temperature dependent optical properties. Several nonlimiting examples are discussed herewith. The refractive index of most pure liquids, mixtures and solutions depends on temperature. Further, liquids containing one or more optically active components display temperature dependent birefringence. Liquids comprising or containing chromophores or fluorophores display temperature dependent absorbance or fluorescence properties. The molecular origins of the temperature dependent changes in absorbance or fluorescence spectra of a particular liquid may arise from one or more of several processes. Examples of thermochromic reactions include ligand substitution reactions such as observed when hexaaquacobalt (II) is heated in mixtures of water and primary alcohols. Other examples include temperature dependent changes in ionization state of chromophores or fluorophors, which are coupled to optical changes. Other examples include processes in which molecular complexes change conformation as a function of temperature resulting in changes in optical properties. Such processes frequently involve changes in the solvent exposure of chromophores or fluorophores attached to polymers. Examples include the temperature dependent conformational changes in proteins and nucleic acids which alter the chemical environment of intrinsic (such as amino acid side chains or covalently bound cofactors in proteins or nucleobases in nucleic acids) or extrinsic (such as noncovalently bound cofactors, or drug molecules) chromophores or fluorophores. Macromolecule conformations may be mediated by small molecule effectors as a function of temperature. Such small molecule mediated effects on optical properties are observed frequently with proteins and nucleic acids but may also be observed in synthetic polymers or carbohydrates an example of which is the changes observed when iodine-starch mixtures are subjected to temperature changes. In the above examples, if the chromophore or fluorophore is optically active or bound to an optically active substrate temperature dependent dichroism or anisotropy may be observable.

Current temperature-dependent spectroscopic and calorimetric methods are laborious and material intensive. In most cases, spectroscopic methods require measuring an optical property of a liquid at one particular temperature preset point and then repeating this measurement for another temperature point until the entire characteristic of the optical property is obtained. Complex sample holding cells are described in the prior art allowing maintaining the temperature of the sample liquid at a desired level. An example of such a cell is described in the U.S. Pat. No. 5,192,910 and includes a sophisticated system for maintaining the same temperature throughout the entire liquid volume. A significant amount of time is needed to achieve and stabilize the temperature of the next measurement point and therefore the entire characteristic can not be obtained quickly. Improvements in sample throughput are therefore needed to make high-throughput thermodynamics practical. A throughput increase of at least two orders of magnitude is required. A need exists in a liquid spectroscopy technology permitting a significant acceleration in optical and thermodynamic characterization of liquids.

Another disadvantage of the temperature dependent optical methods of the prior art is in the discrete nature of measurements. Only certain temperature points are available on the curve and therefore in transitional phases it is quite difficult to obtain information about the property of interest with sufficient resolution without either prior knowledge of the point of transition and its breadth or the time consuming collection of high resolution data outside the range of interest. This also pertains to so-called "zooming", when the property is evaluated most closely and at smallest temperature increments at a temperature from just below to just above the temperature of transition. The need exists therefore for a device and a method of obtaining the optical property of the liquid in a way that accounts for all temperature data points continuously or at sufficient resolution to approximate a continuous measurement from a predetermined first temperature to a predetermined second temperature.

The preferred application of the invention is for liquids containing biological macromolecules. The need exists for a device and method allowing rapid characterization of the thermodynamics of biological macromolecule solutes and their interactions. Such characterizations are useful for drug design, design of probe molecules for use in high-throughput screening, protein engineering, and nucleic acid based diagnostics. Further applications of the method and device in proteomics, genomics and material science are anticipated.

SUMMARY OF THE INVENTION

Accordingly, it is an object of the present invention to overcome these and other drawbacks of the prior art by providing a novel apparatus and methods for rapid all-at-once acquisition of a temperature profile of a temperature-dependent property of a liquid sample or a solid sample contained in a liquid bath or otherwise thermally coupled to a novel holding fixture with predetermined temperature gradient.

It is another object of the present invention to provide an apparatus and a method for obtaining temperature-dependent curve for an optical parameter of a sample for all temperatures continuously from a first predetermined temperature to a second predetermined temperature.

It is another object of the present invention to provide a device and methods for highly effective measuring temperature-dependent optical properties of samples within a short period of time to ensure high throughput and productivity of the measurements.

It is a further object of the present invention to provide a sample holding fixture such as a fixture or a plate with a stable temperature gradient thereacross and with optically transparent windows allowing non-invasive optical interrogation of the sample of interest, such fixture including various internal coatings.

It is yet a further object of the present invention to provide a sample holding fixture with a known temperature profile at any point along its geometry from one end to the other to permit applying a known temperature gradient to a sample of interest in order to collect continuous data for the desired temperature-dependent optical property of that sample.

It is yet a further object of the invention to provide a dismountable holding fixture allowing for placing a solid object inside thereof for rapid acquisition of temperature dependent data.

It is yet a further object of the present invention to provide a method and apparatus for combined evaluation of a sample material using Raman spectroscopy and temperature profile evaluation.

It is a final object of the present invention to provide a method and apparatus for rapid acquisition of temperature dependent data from a sample using total internal reflection fluorescence measurements.

The device and methods of the invention are aimed at evaluating the thermodynamic properties of biological macromolecules and other solution components for which a temperature-dependent transition results in a change in optical properties. The present invention allows collecting an entire thermal melting curve all at once, thereby avoiding several deficiencies of standard methods. This is accomplished by optical or other examination as a function of position of a sample in a fixture designed to produce a stable temperature gradient. The optical observable measured at any position is related easily and directly to the temperature at that position, thereby allowing reconstructing of a thermal melting curve from data collected in just a few seconds or minutes. The method of the invention speeds the process of data collection up to 100 fold or more. Besides the advantage of greater throughput, the technology of the invention permits conducting of a number of experimental protocols that cannot be accomplished by conventional instrumentation.

The general concept behind the method of the invention is to place a liquid or solid sample of interest in or on a holding fixture with optically transparent windows designed to establish and maintain a stable temperature gradient across the liquid. In case of a solid sample, it is envisioned to place it in a liquid within the holding fixture or in direct contact with the holding plate. The sample is examined optically or using other methods as a function of position in the temperature gradient holding fixture. The observable parameter measured at any position is related easily to the temperature at that position. A thermal melting curve or temperature profile, defined as an observable versus temperature, can be obtained from data collected in a just few seconds or minutes along the entire holding fixture. The interrogating light may comprise a single wavelength, multiple wavelengths, or a broad band of wavelengths. The optical observable may be measured at one or more specific wavelengths or may comprise a spectrum measured over a range of wavelengths. The optical observable may include but not be limited to absorbance, fluorescence, and refractive index. Use of polarized light permits applications using linear or circular dichroism, birefringence, optical rotary dispersion, or fluorescence anisotropy. The data collected (observable versus temperature) may be analyzed for properties or in the preferred embodiment used to extract thermal and thermodynamic information about the investigated liquid.

This method also opens up an opportunity to conduct measurements of the temperature dependent properties with adaptively changing values of the temperature limits of these measurements.

The invention principally utilizes the linear thermal propagation property of bars or plates made of materials having high thermal conductivity such as many metals. Preferably, one of the three axes of these bars is significantly longer than the other two. When differing amounts of heat are applied or absorbed from the ends of such a bar, a gradient of temperature results. Temperature sensors at the ends of the bar are used for feedback control of the temperatures at the ends of the bar. Because the temperature of the ends of the bar can be controlled precisely, a stable temperature gradient can be maintained from a first temperature at one end to a second temperature at the other end. The temperature at any point in the bar can be related directly to the distances from the two ends and their temperatures. Therefore, the temperature coordinates are mapped directly to spatial coordinates. A fixture can therefore be constructed by hollowing of the bar. The temperature of the space within the hollowed bar will be determined by the surrounding material of the bar. Convection is minimized by constructing the device with a large axial ratio; typically with the long axis being about 20 times or more greater than the shorter axes. A holding fixture is therefore constructed with two quartz windows that permit ultraviolet and visible light to pass through the fixture. The quartz or glass window material is much less thermally conductive than the metal body of the fixture; therefore, a temperature gradient can be established and maintained by control of the temperature at the ends of the metal fixture body. When the fixture is filled with a liquid of interest and the temperature gradient applied, the optical properties of the liquid or solution contained therein are readily measured as a function of temperature.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 4A is an exploded view of a dismountable version of the holding fixture of the invention, FIG. 4B is a general view of an alternate design of the holding fixture, namely using a solid plate, FIG. 4C is a further improvement of the previous figure in which the plate contains multiple channels or strips designed to accept a number of samples at the same time, FIG. 6 is a side view of the first configuration of the thermoelectric elements of the invention, FIG. 7 is a side view of the second alternate configuration of the thermoelectric elements of the invention, FIG. 8A is a general view of the alternated configuration of the system in which the holding fixture is equipped with a mirror on one side and the optical system is provided on the opposite side of the fixture, FIG. 8B is another alternate configuration adapted for combining temperature dependent data collection with Raman spectroscopy, FIGS. 8C and 8D show schematically an embodiment adapted for total internal reflection fluorescence measurements, FIG. 9 is a schematic side view of the optical system of the invention.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
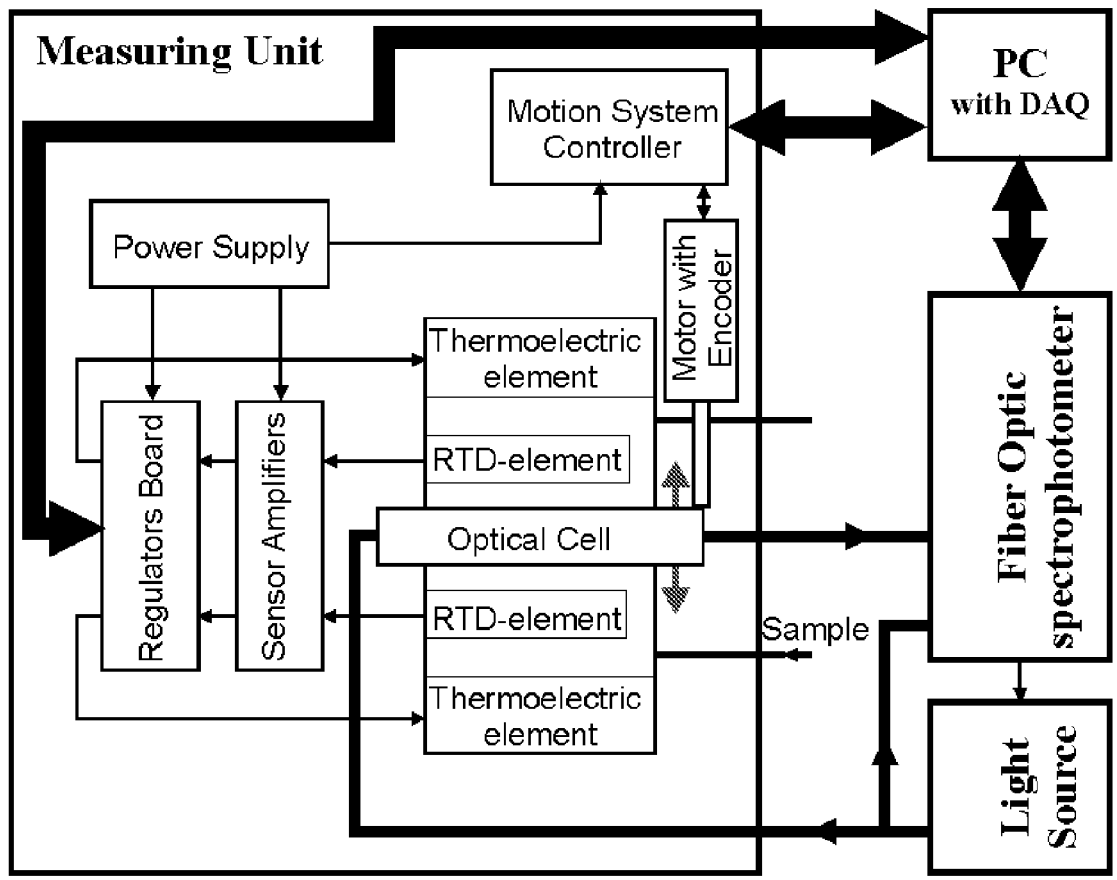
FIG. 1 is a functional schematic of a device of the invention including a temperature gradient holding fixture with moving optical fibers interfaced to a commercially available spectrophotometer.

Generally speaking, the device of the invention consists of the following major systems shown on FIG. 1:

A holding fixture for containing the liquid of interest,

A temperature control system to create and maintain the desired temperature gradient across the holding fixture, An optical or another system to interrogate the liquid of interest and obtain desired optical properties at one or preferably more points of measurement having a well defined geometrical position relative to the two points defining a temperature gradient across the fixture, An optional motion drive positioning system to place the optical system at the desired point along the holding fixture (if the optical system can not cover the entire length), and An overall control and data acquisition system such as a personal computer to oversee the entire process automatically and collect data.

Description of the Holding Fixture Embodiments

Figure 3:
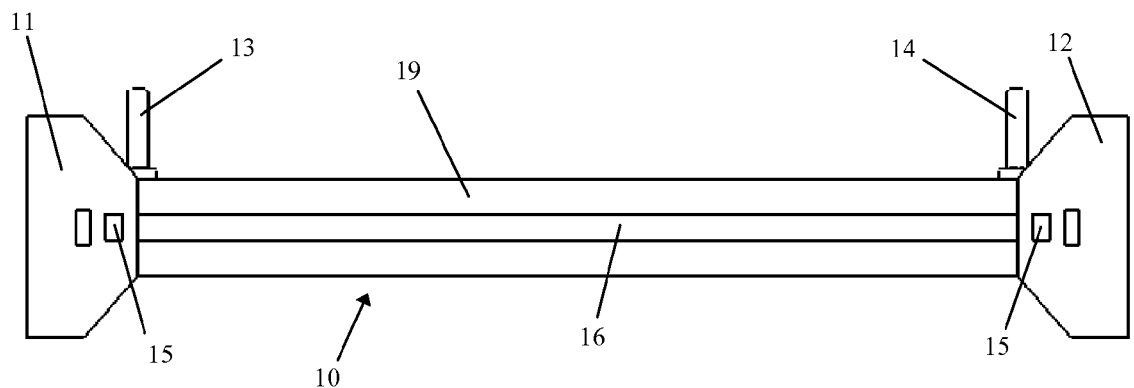
FIG. 3 is a side view of the holding fixture of the preferred embodiment of the invention.
Figure 4:
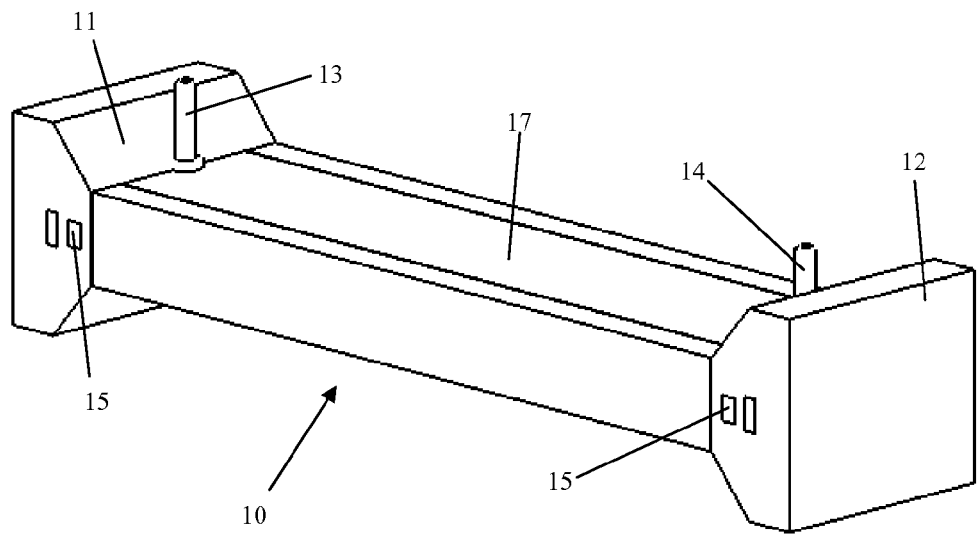
FIG. 4 is a general view of the same with an alternate position of the optical window.
Figure 4:
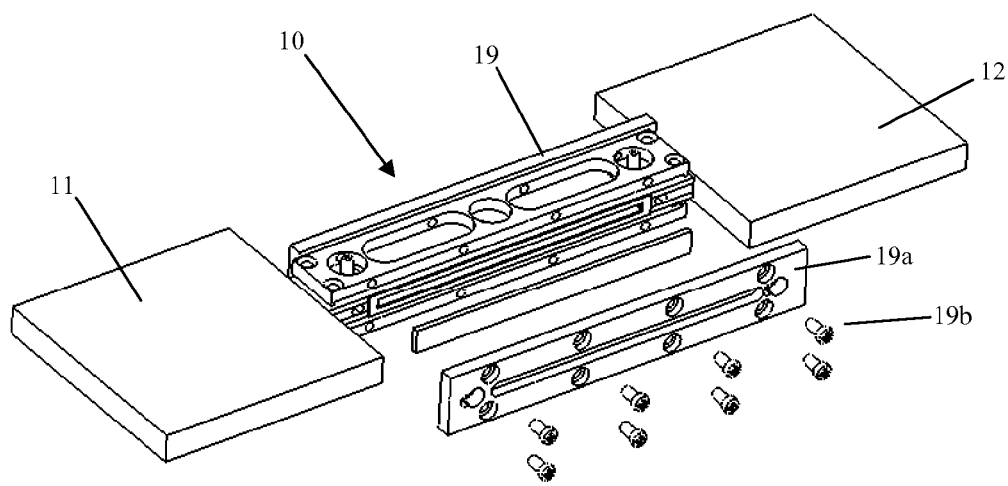
Figure 4:
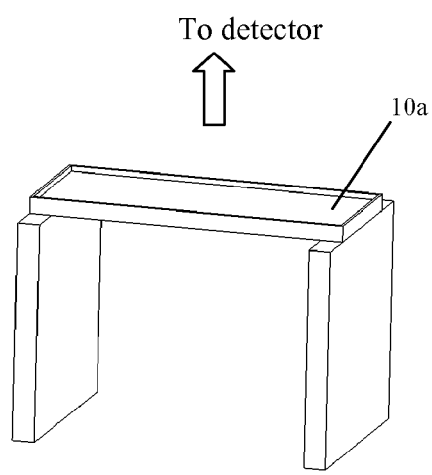
Figure 4:
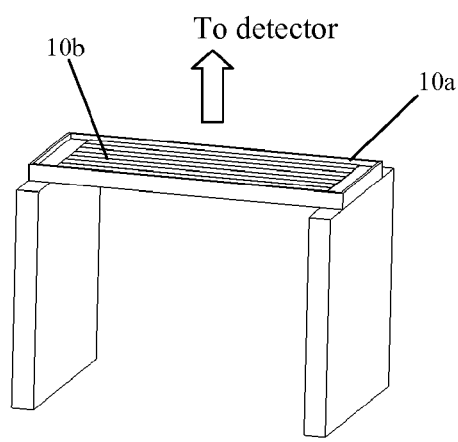

The critical innovative element of the device is the holding fixture 10 shown on FIGS. 3 and 4. The term "fixture" includes a traditional holding cell as described in the parent application as well as other variations such as a plate as described in more detail below. Its design is based on a predictable temperature conductive property of a rectangular bar made of highly thermo-conductive material such as metal. To be of practical value, the material of the fixture should have its thermal conductivity level of at least about 100 W/mK. Gold has high thermal conductivity at about 317 W/mK at 300°K. Another advantage of gold is its chemically non-reactive nature. Copper is another most preferred metal that can be used for making the holding fixture due to its known high thermal conductivity of about 401 W/mK. Other preferred metals include silver (429 W/mK), aluminum (237 W/mK) or combinations thereof, optionally covered with a non-reactive coating.

The holding fixture 10 is constructed of a single piece of metal or two pieces fused or connected so as to maintain good thermal contact at the ends. The body of the fixture 19 extends from a first end 11 to the second end 12. The shape of the ends 11 and 12 is adapted to fit into the temperature control system (described later in detail) so that effective thermal conductivity is obtained. Optically transparent polished quartz windows 16 on the side of the fixture (or alternatively on top of the fixture as shown on FIG. 4 and depicted as position 17) are incorporated into the fixture 10 to form the internal sample holding cavity therein. Optional baffling may be used for a specific configuration of the window as shown on top on FIG. 4 to prevent convection. Either thermoplastic cement or a gasket provides the interface between the quartz window and the metal fixture body. It is important to match the properties of this material to that of the fixture itself to avoid differences in the thermal expansion coefficients for the different materials. To avoid convection in the vertically mounted fixture, it is preferred that the fixture be mounted exactly vertical and that the opposing sides be exactly parallel. Ports 13 and 14 are included for introduction and removal of liquid solution. Light reference holes 15, one open and one closed, are placed at each end. The fiber optic spectrophotometer requires a measurement through a clear path and a blocked path for calibration of the photo-detector response.

Convection and concomitant redistribution of temperature within the fixture are desirably minimized by constructing the device with a large axial ratio; typically with the long axis is made about 20 times or more greater than the shorter axes. It is also preferred to position the fixture strictly vertically and have a higher temperature at the upper end.

The device can be made very small relative to the size of typical spectrophotometer cells used in temperature controlled optical spectroscopy. The entire device can be as small as 10 mm in length, with a width of 0.5 mm and a depth (path length in an absorbance experiment) that can be from 1 to 10 mm. The potential for construction of the device on this small scale opens a number of possibilities for illumination and detection that are not easily realized in larger devices. In addition, the small size of the device permits very rapid thermal equilibration and thus radically reduces the time required for collecting temperature dependent data.

Optionally, other configurations of the holding fixture design are contemplated. They include at least one location at which the temperature can be maintained at a predetermined level or adjusted based on a predetermined heating or cooling profile.

An improved holding fixture configuration is shown on FIG. 4A. A dismountable fixture 10 is shown that can be used to hold solid samples surrounded by liquid or replace one or more windows with an investigated material or with a window coated by an investigated material or a window coated by a material that interacts with the investigated material. The fixture 10 can be removed from the device, disassembled, reassembled and replaced in the device.

The dismountable fixture 10 includes at least two parts, namely a main body 19 and a detachable window portion 19a, which can be removably and sealably attached to the main body 19 for example by a set of screws 19b. The use of gaskets including self-adhesive gaskets or other alternative sealing methods is contemplated to isolate the sample material contained within the holding fixture 10.

The use of a dismountable fixture allows evaluation of solid samples bathed in liquid or substitution of variously coated windows or windows of different materials. As in all applications of temperature profile spectroscopy, this variation uniquely provides for rapid acquisition of temperature dependent data.

FIGS. 4B and 4C illustrate a further improvement of the holding fixture concept by introducing a concept of a holding plate 10a used in place of a holding fixture 10. The plate 10a may be smooth (as shown on FIG. 4B) or may include channels or wells 10b preferably oriented along the direction of the temperature gradient (as shown on FIG. 4C). The plate may be transparent for detection methods requiring light to pass through it. The plate may be opaque if the detection method does not require light transmission. The thin layer of sample liquid may be placed on the plate or in its channels or wells and it may also be exposed to atmosphere or covered with an optional window (not shown) or an immiscible lower density liquid.

Alternatively, a separate secondary plate containing the liquid sample may be placed in thermal contact with the main plate (not shown). The secondary plate may have wells or channels incorporated therein and oriented in parallel with respect to the direction of the temperature gradient. The secondary plate may be coated with a layer of material that interacts with the investigated liquid or solution. That interaction may be observable optically. The coating material may vary in composition or concentration as a function of position. This embodiment also provides the means to advantageously use removable or disposable secondary plates which eliminates any potential problems caused by inadequate cleaning and sample crossover.

A further yet improvement of the present invention is the use of thin film (optionally self-adhesive), which serves the same function as channels described above, see FIG. 4C. This film 10b can easily be made disposable. The film may comprise or be coated with a material that interacts with the investigated liquid or solution. That interaction may be observable optically. The coating material may vary in composition or concentration as a function of position. Advantageously, the material of this film may include fluorescent or other optically observable labels to investigate solutions or materials that interact with fluorescent compounds included in a liquid in contact with the film. Tens, hundreds, and even thousands of strips or spots comprising different materials can be formed on the film.

In a further yet variation of the device of the present invention, multiple independent parallel holding fixtures may be constructed as if from a single block and be controlled by common heating and cooling elements and controller. Alternate window geometries may be constructed to facilitate fluorescence or refractive index measurements. Placing the windows on the top and bottom of the fixture would require baffling to prevent convection. A circular arrangement in which the circle is interrupted by the heating and cooling elements may be also employed. In a circular configuration the windows may be arranged such that the optical interrogation is perpendicular to the plane of the circle, or with the light source inside and detector outside the circle, or with the detector inside and light source outside the circle. This configuration will also benefit from baffling to avoid convection.

The material that is in contact with the investigated solution must not interact with it chemically. To prevent interaction of the holding fixture body with the solution, the surface of the fixture is optionally coated with a non-reactive material. Parylene C (poly(monochloro-p-xylylene)) or a similar polymeric material or gold provides a satisfactory barrier. The Parylene C polymer has a number of favorable properties for the temperature gradient optical holding fixture application. It is applied as a gas at ambient temperature by vapor deposition polymerization techniques. This permits thin, uniform coating of irregularly shaped objects. The material melts at 290 C and has excellent water barrier and metal adhesion properties over a wide range of temperatures. Proteins do not stick readily to this material, which is used to coat medical implants, catheters and other medical devices as well as printed electronic circuit boards. The inside of the holding fixture also may be coated with a thin layer of gold, which has been used to manufacture high-sensitivity calorimeter cells.

The fixture may be alternatively constructed from gold or other chemically nonreactive metals with high thermal diffusivity. High thermal diffusivity provides rapid formation of stable temperature gradient while nonreactivity eliminates influence of liquid-fixture interaction on optical data. Aluminum alloys form a thin protective surface layer by anodization. Anodized aluminum is very inert, extremely hard and mechanically stable. In place of Parylene, the surface of the fixture may be coated by gold or other nonreactive metals, or a layer of a different surface bound material, comprising polymers, or small molecules such as a self assembled monolayer. Such self-assembled monolayer can be based on functionalized alkanes such as alkylsiloxanes, fatty acids, alkanethiolates, and other compounds known in the art.

Construction of the fixture with different metals allows for optimization of the thermal response of the device and selection of materials that are nonreactive with any particular liquid of interest. As in the case of Parylene, the use of coatings allows use of materials to construct the fixture that might otherwise be incompatible with the materials of interest, either by reaction or by surface interactions.

Optionally, two or more optical holding fixtures can be constructed in a stacked array with common thermoelectric (Peltier) devices and heat sinks. The fixtures can be illuminated simultaneously as well. The number of fixtures is not limited. Each of the fixtures can be filled independently. The body of the apparatus of the invention in that case will have a number of discrete chambers corresponding to the number of fixtures. A single pair of windows can be used to form two of the sides of each sample chamber with the top and bottom formed by the body of the fixture. As with the single chamber fixture, gaskets, with gaps corresponding to each chamber or thermoplastic cement is used to seal the window to the body and to relieve stress in the windows. This multiplexing permits several experiments to be conducted simultaneously. For example, a study of the pH dependence of a transition can be completed with one round of fixture filling and data collection as opposed to sequential filling, data collection, and cleaning of a single fixture device.

The temperature at the center ($T_c$) and the first and second temperatures ($T_l$, $T_u$) at the lower and upper ends of the fixture are measured. Due to imperfect insulation of the holding fixture from the environment, some (and sometimes significant) deviations of temperature at the center of the fixture from that expected for a linear temperature gradient are observed. The magnitude of the nonlinearity depends on the temperature range spanned by the gradient and its relation to the ambient temperature. Because the primary issue is not the linearity of the gradient but its stability, a parabolic approximation based on temperatures measured at the center and at each end of the fixture is sufficient to correct for the nonlinearity of the gradient.

The three measured temperatures are used to calculate the temperature at any position x by $T_x = ax^2 + bx + T_l$, where $a = (T_u - T_l - bL)/L^2$, and $b = (4T_c - 3T_l - T_u)/L$, $L$ is the length of the fixture.

Description of the Temperature Control System Embodiments

Figure 5:
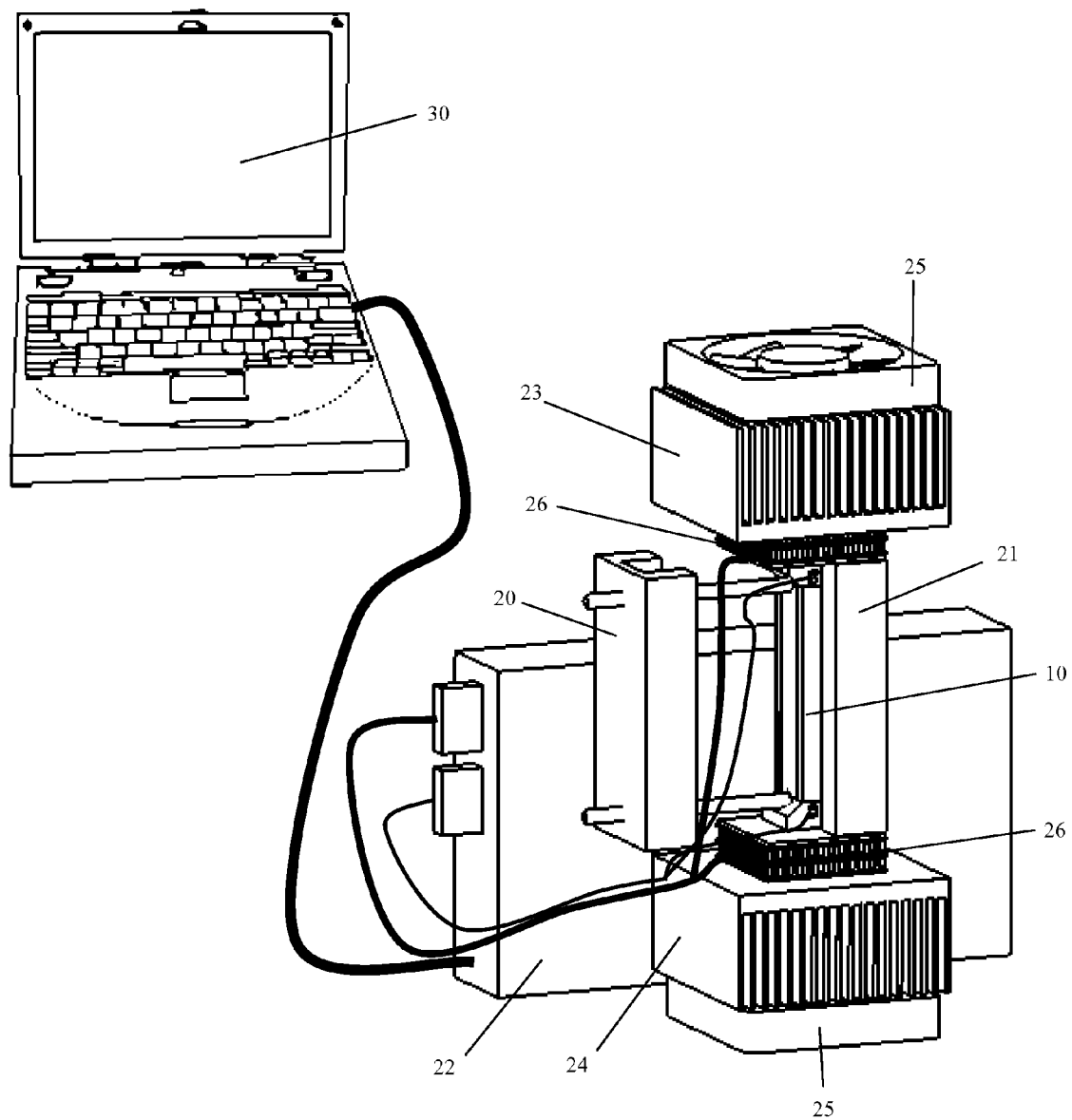
FIG. 5 is a general view of the temperature control system of the invention.

The temperature control system equipped with the temperature gradient optical holding fixture 10 of the invention are shown on FIG. 5. The preferred vertical orientation is shown. The temperature at each end of the fixture 10 is controlled independently in a preferred range of between 0 and 100 C. A wider temperature range is also contemplated by using refrigeration systems to cool off one or both ends of the holding fixture 10 if needed. Thermal insulation halves 20 and 21 are used to isolate the fixture 10 from the environment (FIG. 5 shows one half 20 removed from the fixture 10). Multistage Peltier effect thermoelectric elements 23 and 24 provide heating or cooling, as necessary, to the ends of the fixture. Other methods of applying heat or cold are also contemplated and include known heaters and coolers. Temperature sensors 26 (such as RTD elements) monitor the temperature at each end of the fixture 10. When electrical current is applied to a Peltier element 23 and 24, one surface is heated and the other is cooled. Therefore, heat sinking is critically important to the design. Heat sinking is accomplished by arrays of metal fins and small fans 25 placed at each end of the device or alternately by circulating liquid cooling with a radiator or refrigerator placed away from the temperature gradient holding fixture 10. The temperature control unit enclosure 22 contains the power supply, temperature regulation circuitry, and amplifiers for the temperature sensor signals. The temperature set at each end of the fixture 10 is determined by an electrical signal originating in the computer 30, which in turn is under software control.

FIG. 6 shows a configuration of the holding fixture 10 of the invention with the thermoelectric elements 23 and 24 located across the lower and the upper end of the fixture. In an alternate configuration shown on FIG. 7, the thermoelectric elements 23' and 24' are aligned with extended ends of the holding fixture 10 to increase the efficiency of heat transfer.

The design of the optical system will now be described in detail. While any optical property can be monitored in a temperature gradient optical holding fixture of the invention, the preferred embodiment is a device to monitor absorbance. A commercial fiber optic spectrophotometer permits the measurement of the entire ultraviolet/visible (UV/Vis) absorbance spectrum from approximately 200-800 nm in a fraction of a second. It is comprised of a tungsten/deuterium light source and a self-contained spectrophotometer interconnected by optical fibers 50. The spectrophotometer is interfaced to and controlled by the personal computer 30 shown on FIG. 8.

Figure 8:
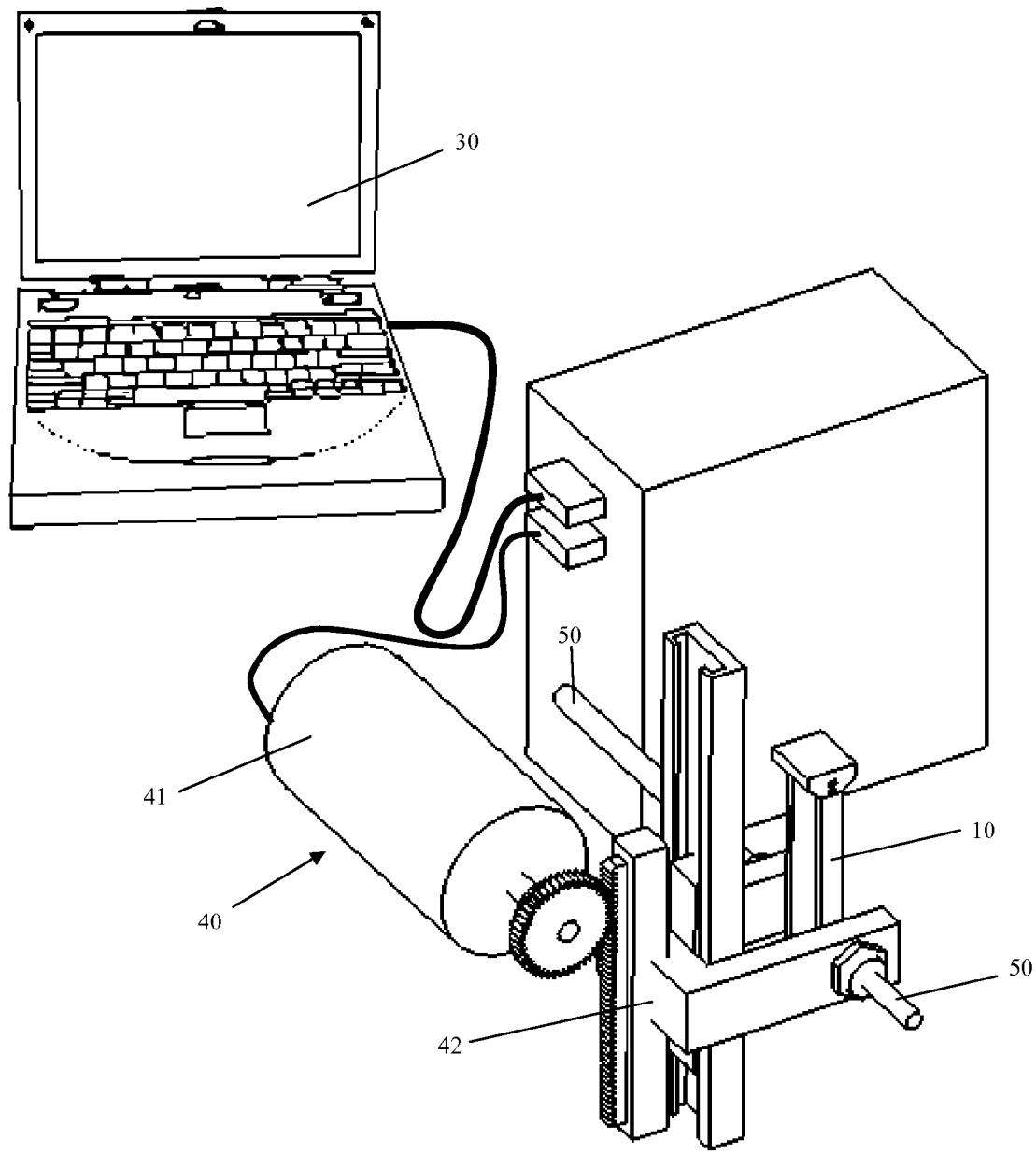
FIG. 8 is a general view of the motion drive system of the invention.
Figure 8:
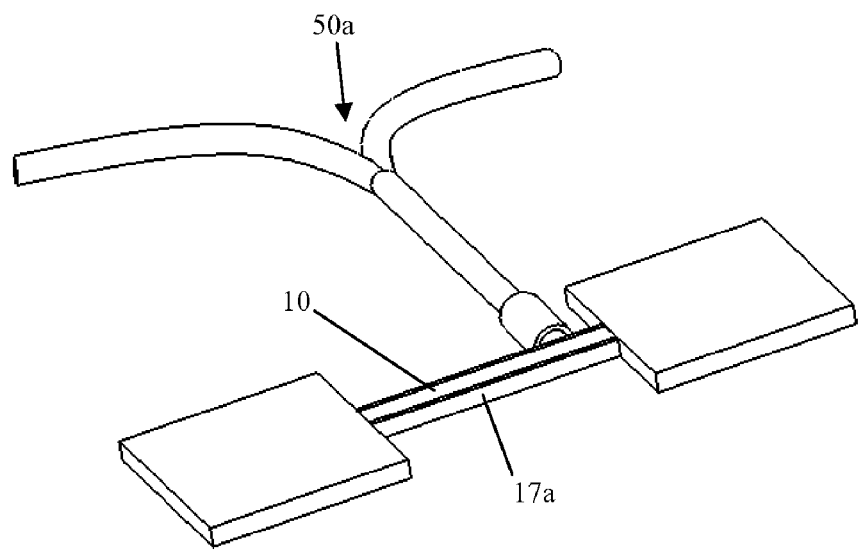
Figure 8:
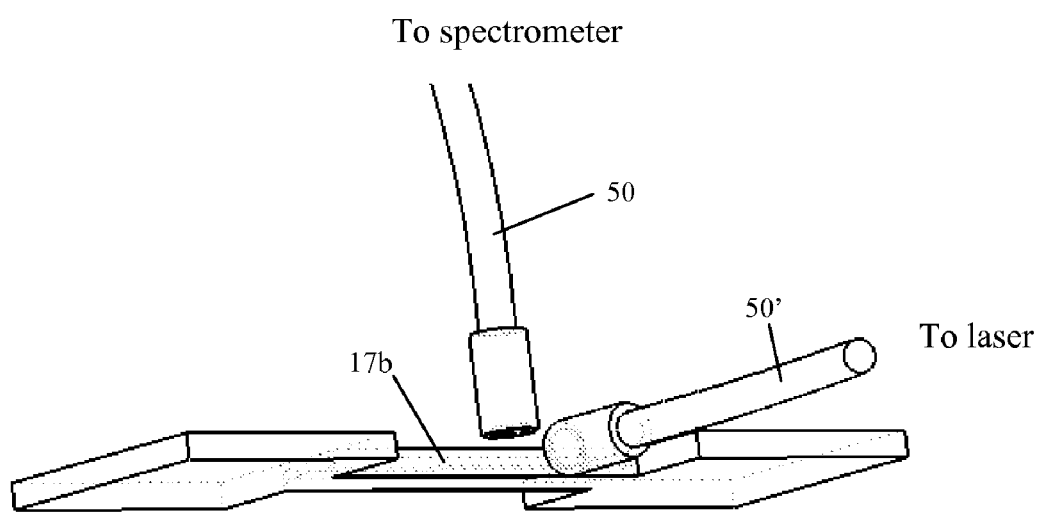

In order to collect absorbance data as a function of temperature, the optical fibers 50 must be aligned and positioned accurately along the length of the optical holding fixture 10. Three methods are contemplated to deliver light to the sample fixture 10 and to collect the light transmitted through the sample. In the first method, the illuminating and collecting optical fibers of the spectrophotometer are mounted on a "U" shaped stage so they are permanently aligned (FIG. 8). The stage moves so that the temperature gradient holding fixture is located between the arms of the "U" shaped stage and the light passes through the fixture. A computer-controlled, high-precision, encoded motor 41 and a high-precision, gear-driven, positioning system 42 is forming the motion drive system 40, which is employed to align and move illumination and collection fibers 50 relative to the temperature gradient optical holding fixture 10 (see FIG. 8). A computer-controlled motor 41 moves the stage in defined steps parallel to the long axis of the temperature gradient optical fixture 10. Spectral data are collected at each step. In this fashion, the entire spectrum is collected as a function of position (and thus temperature) very rapidly relative to a conventional spectrophotometer. A 3-dimensional (absorbance vs. wavelength vs. temperature) melting profile results.

In a second method, an array of illuminating optical fibers may be arranged in fixed position along the length of the fixture; a parallel array of collection fibers is aligned to collect light transmitted through the fixture. This embodiment allows for simultaneous collection of optical data as a function of position and obviates the requirement to move the optical fibers. The light from the source is preferably focused onto a bundle of optical fibers. The fibers terminate at a linear array of microlenses made of material transparent across the desired illumination spectrum. A second microlens array collects the light that has passed through the sample fixture and focuses the light from each lens onto a fiber. With some other types of optical fibers, there is no need for a microlens array and the fibers may be used directly to illuminate and collect the information from the fixture. A CCD camera or array of CCD elements images the other end of the collection fiber bundle. Alternatively, the array of collection fibers is omitted and the transmitted light is imaged directly from the fixture.

In a further yet configuration of the third method (not shown on the drawings), the optical fibers are fixed in their position and the holding fixture 10 is moved along the fibers to allow the collection of required data.

Several options are available for the illumination system of the holding fixture of the invention and the detection of the transmitted light. In all cases, a first lens 51 and a mask 55 are used to collimate the incident light from a fiber 50 and a second lens 52 is used to focus the light transmitted through the sample in the fixture 10 onto the end of the collection optical fiber 50', see FIG. 9. A front view of the mask 55 is shown below the diagram indicating a preferred configuration for forming rectangular beam profile through the opening 53. In addition, the optical fiber may be a bundle of optical fibers. In all cases, multiple sample channels can be accommodated although only single channel applications are illustrated herein.

In the simplest embodiment, a band pass filter is used to select a narrow band of incident light. For collecting spectra over a range of wavelengths, a monochromator is used to scan over the desired range of incident light. The light transmitted through the sample is collected and directed to a detector where it is quantified.

Alternatively, the sample containing holding fixture can be exposed to the entire light spectrum produced by the lamp with wavelength discrimination subsequent to transmission through the sample. This illumination may occur at a single point along the temperature gradient or over the entire gradient. The device using single point illumination employs a moving stage to position the illumination and collection optical fibers opposite each other straddling the optical path of the fixture. The fibers scan the fixture parallel to the temperature gradient. The positioning and alignment of the optical fibers relative to the temperature gradient fixture is a critical feature of the design. The collected light is directed to a commercial fiber optic spectrophotometer, in which the light is spread by a grating across a linear CCD detector.

The device illuminating the full range of the gradient employs an array of fixed position optical fibers, which illuminate multiple points along the temperature gradient. A parallel array of collection fibers directs the transmitted light to the detector, which is a 1 or 2-dimensional CCD array or camera.

In another embodiment of the device, illuminating the full range of the gradient employs a single collimated light beam shaped to span the length of the temperature gradient.

In a further embodiment of the device, illuminating the full range of the gradient omits the collection fiber array and detects the transmitted light with a 1 or 2-dimensional CCD array or camera.

Another embodiment of the multiple fixed position illumination/collection fiber arrangement directs the transmitted light to strike a grating or prism that displays the diffracted or refracted wavelengths in one direction and the temperature gradient in the other direction on a 2-dimensional detector (CCD array) or camera. Collection of the entire temperature profile spectrum (A vs. λ vs. T) is achieved in one exposure.

As an alternative to CCD detectors, some embodiments may employ photodiode or photodiode array or photomultiplier detection.

Filters or prisms can be used to illuminate the sample with polarized (linearly or circularly) light at some wavelength or set of wavelengths and the absorbance measured. A halfwave plate is interposed between the polarizer and the sample, which reverses the direction of polarization, and again absorbance is measured. The difference between the two-absorbance measurements leads to a value for the dichroism (linear or circular).

Similar to the dichroism measurements, quarter wave plates can be used to measure birefringence or optical rotatory dispersion at selected wavelengths using the temperature gradient refractive index cell technique. Alternatively, refractive index measurements could be made using specialized refractive index sensors and a specially modified rectangular temperature gradient optical fixture.

A temperature gradient fluorescence holding fixture can be constructed by placement of a third window normal to the incident light, that is, on the side of the fixture. The detection occurs normal to the incident beam. A second detector in line with the incident beam, as in the absorbance fixture, is included to monitor simultaneously the absorbance of the sample. Here again an array detection scheme is used preferably to collect data from the entire fixture simultaneously. An alternative embodiment for fluorescence measurements employs the temperature gradient holding fixture designed for absorbance measurements equipped with filters to select for the fluoresced light eliminating the entire transmitted incident light.

In the embodiment for absorbance measurements, the windows in the holding fixture have been mounted so as to be parallel. Mounting the windows so that the long sides are at an angle permits the measurement of refractive index, making the fixture to behave as a prism.

Further improvements to the present invention are illustrated on FIGS. 8A through 8D. FIG. 8A shows a version of the device using a holding fixture 10 equipped with a mirror 17a positioned in place of a second window 17. In that case, a bifurcated optical fiber bundle 50a is deployed with a first part of the fiber delivering light to the temperature gradient fixture 10 and a second part of the fibers receiving light from the fixture 10. Light from the first part of the fiber bundle 50a will pass through the sample and will be redirected by an opposing mirror 17a or an optional prism back through the sample to the second or receiving part of fibers of the bundle. The received light will be directed to the detector. This arrangement reduces the sample volume by half for a given optical pathlength and simplifies the design of the apparatus.

FIG. 8B shows an arrangement of the apparatus adapted for use with Raman spectroscopy. Raman spectrometer can be used as investigation method combined with the temperature dependent spectroscopy technique. Inelastic scattering of monochromatic light, known as Raman scattering, will be detected as a function of position in the temperature gradient optical holding fixture. Raman spectroscopy is a spectroscopic technique used in condensed matter physics and chemistry to study vibrational, rotational, and other low-frequency modes in a system. Raman Spectroscopy combines the finger-printing advantage of mid-IR spectroscopy with the ease of use and remote, non-invasive capability of near-IR spectroscopy, to make it a very versatile tool for quantitative or qualitative analysis.

Raman spectroscopy is sensitive to vibrational and rotational modes of molecules in the liquid. Energy is exchanged between the photons and the vibrational and/or rotational modes of the molecule the scattered light being shifted to either higher or lower wavelength relative to the incident light. A laser in the visible, near infrared, or near ultraviolet range will serve as light source. Optical fibers 50 and 50' with respective collimators can be used to send the light to the temperature gradient fixture 10 and to send the scattered light to detector.

Light from the illuminated sample will be collected at an appropriate angle to the incident beam with wavelengths close to the laser line filtered out. A preferred angle is 90 degrees but other angles can be used as known in the art. A CCD spectrophotometer will be used to measure the spectrum of Raman scattered light. Alternatively, a monochromator will disperse the light which will be detected by a photomultiplier or a CCD camera. A U-shaped window 17b can be advantageously used in this embodiment for a broader range of angles between the illumination and Raman spectroscopy.

FIGS. 8C and 8D show the embodiment of the invention in which the methods of obtaining temperature dependent data described above are implemented in the mode of total internal reflection fluorescence measurements. Light 65 is directed from an objective 60 equipped with the objective lens 61 through the immersion oil 63 to a window of the temperature gradient holding fixture 10 covered with a cover glass 62 at the critical angle necessary for total internal reflection. Total internal reflection fluorescence exploits the properties of an induced evanescent wave in a limited region of the sample (usually less then 200 nm into the sample) immediately adjacent to the interface between two media having different refractive indices. Fluorescence of fluorophores near the surface of the window is observed as a function of position relative to the temperature gradient. Reflective light 66 is then recorded.

This technique is commonly employed to investigate the interaction of molecules with surfaces, an area which is of fundamental importance to a wide spectrum of disciplines in cell and molecular biology.

For light detection and analysis, the use of the fiber optic spectrophotometer has a number of significant advantages. Because a collimated beam of light emerges from the device, the need for elaborate optical design is obviated. The optical problem is reduced to orienting the resultant beam normal to the window of the temperature gradient holding fixture, masking of the beam, and alignment of the collecting lens with the beam. This is illustrated in detail on FIG. 9. The mask 55 will permit a narrow beam (e.g. 1 mm high by 0.5 mm) wide to strike the sample. The width of the beam is the determining factor in the temperature resolution of the device.

An integrated software package to control the temperature gradient in the fixture, the positioning of the optical fibers were applicable, and the collection, recording, display and analysis of optical property data complete the device.

Figure 10:
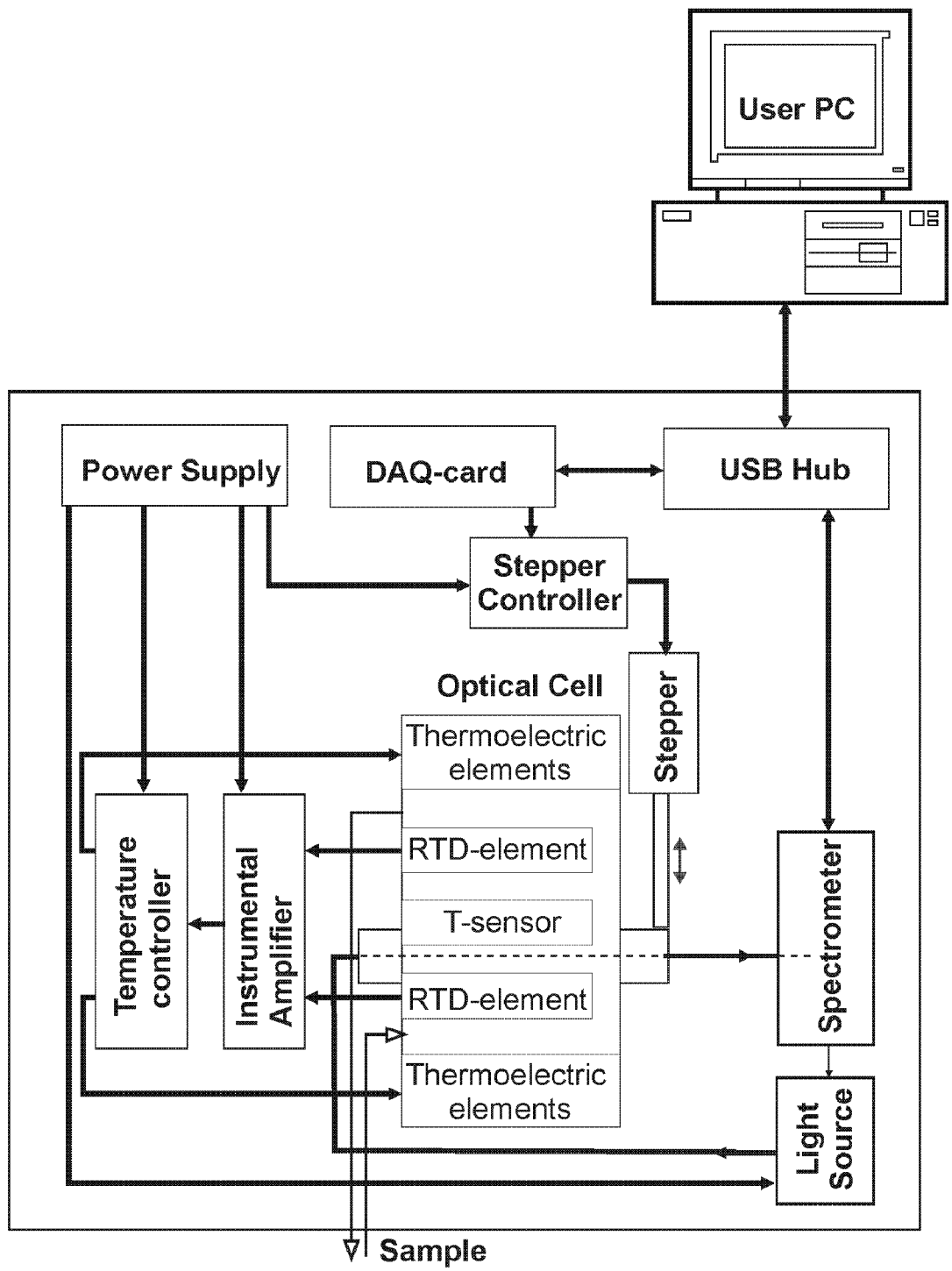
FIG. 10 is a general block-diagram of the alternate configuration of the invention, and finally

The use of a stepper motor is shown on FIG. 10 as an alternate arrangement for the system of the invention.

Figure 11:
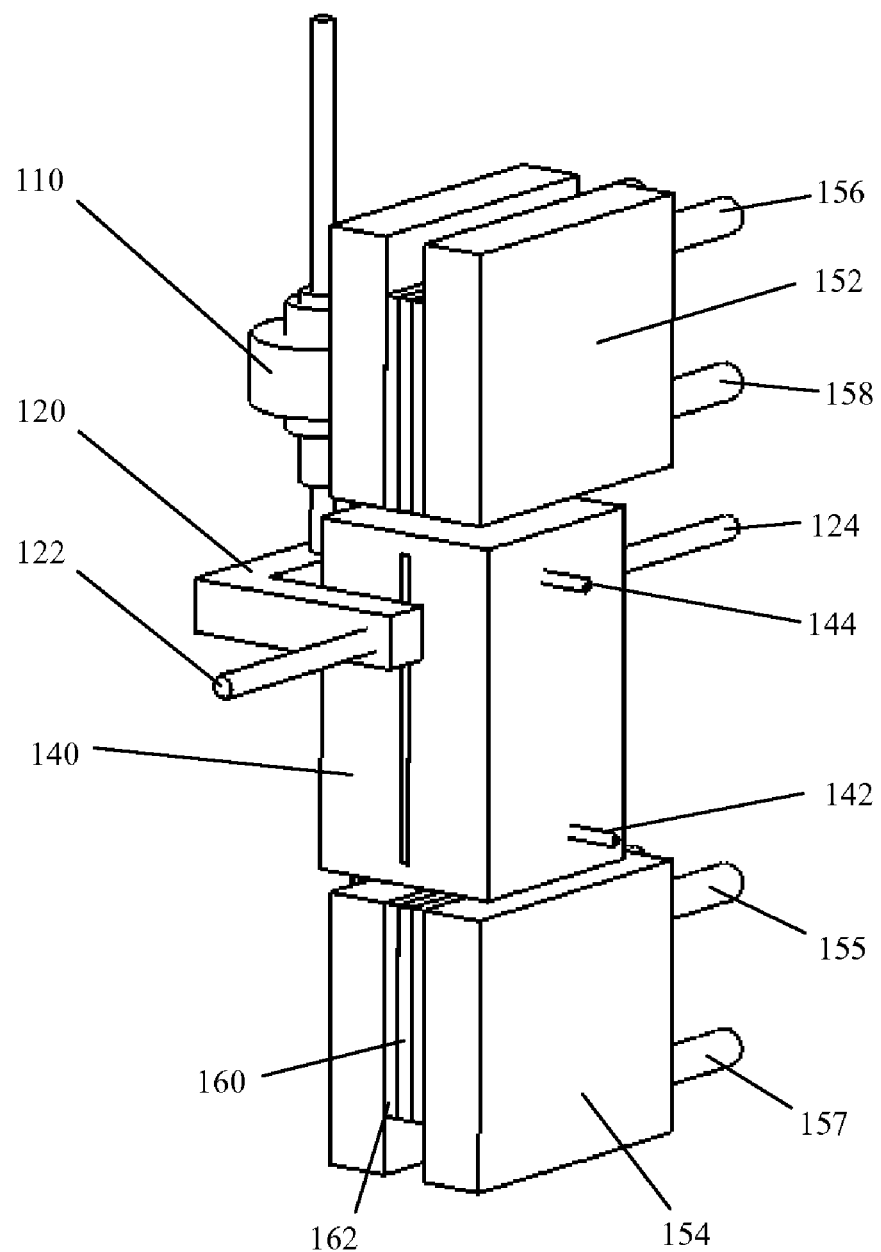
FIG. 11 is a side view of the holding fixture and the thermoelectric system of the embodiment shown schematically on FIG. 10.

Another alternate configuration is shown on FIG. 11 and includes a heat shield 140 containing a fixture of the invention, which can be filled with liquid of interest through an inlet 142 and emptied through an outlet 144. A U-shaped frame 120, which can be moved up and down by a linear actuator 110, supports the illuminating 122 and receiving 124 optical fibers. The top 152 and the bottom 154 liquid heat exchangers maintain the desired temperature gradient. Hot or cold liquid is circulated through the ports 156 and 158 of the top heat exchanger 152 or through the ports 155 and 157 of the bottom heat exchanger 154. A heat conductor 162 is located in the middle of either heat exchanger and is optionally surrounded by a pair of thermoelectric modules 160 to control its temperature. This version of the device works in a way similar to others as described in more detail above.

Figure 2:
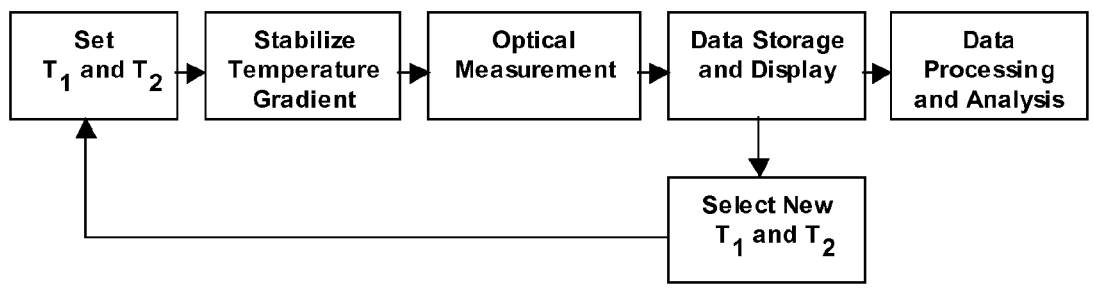
FIG. 2 is a block-diagram of the steps of the basic method of the invention.

In use, the apparatus of the invention provides unique advantages in measuring optical properties of a liquid of interest. A variety of experimental protocols are possible with the apparatus and the methods of the present invention. Common to all of these methods is a basic sequence of steps outlined on FIG. 2. The temperature gradient is defined by the temperatures at the first and second ends of the fixture, $T_1$ and $T_2$. The lower temperature is arbitrarily assigned to $T_1$. The temperature gradient is described by $\Delta T = T_2 - T_1$. Note that the temperature resolution varies with $\Delta T$.

By manipulation of $T_1$, $T_2$, and $\Delta T$, a number of unique experiments are possible. The temperatures and all of the optical measurements are controlled by software on a dedicated personal computer 30. All experiments are variations of a basic procedure: (1) set $T_1$ and $T_2$; (2) wait until temperature gradient is stable; (3) make optical measurements and (4) save data; (5) if experiment is not complete, select new $T_1$ and/or $T_2$ values and return to step 1; (6) analyze the data to extract information on optical properties and/or $T_m$ (the temperature at which the transition is half complete) and thermodynamic parameters of the solution.

Table 1 exhibits unique experiments using the methods of the invention. To collect the same data using a conventional spectrophotometer would in each case require significantly longer time and in some cases a series of distinctly separate experiments.

The experimental protocols are controlled by software. Depending on the experiment, the operator would provide a small number of input parameters, which may include $T_{min}$ and $T_{max}$, the number of steps (number of $T_1$, $T_2$ pairs), the $\Delta T$ value (the breadth of the temperature gradient), $\delta T$ (shift of the window between steps) particular $T_1$ and/or $T_2$ values, or some subset of these. These protocols may be used independently or in combination. The first three experimental methods are deterministic in that the operator defines a set of parameters that are used to define a specific series of temperature windows for data collection. The remaining 3 experimental methods are adaptive in that the breadth of the window and the number of steps are adjusted based on the data recorded for the previous temperature window. In this way, the software can "home in" on the transition region of the temperature gradient. Of these, the adaptive window and zooming window methods must be applied to reversible transitions whereas the zooming window with fixed $T_1$ method can be used for irreversible processes. Assuming that the liquid of interest is similar to water in its dependence of density on temperature, in order to avoid convection with the fixture in the vertical orientation, $T_1$ must not exceed the temperature at any point in the fixture. Alternately, when there is a need to evaluate water-like liquid at low temperature, the opposite arrangement might be preferred.

TABLE 1

| Temperature Gradient Measurement Methods | | | |
|---|---|---|---|
| Experimental Method | $T_1$ $T_2$ | $\Delta T$ | $\delta T$ |
| Single Window | $T_{min}$ $T_{max}$ | $T_{max} - T_{min}$ | — |
| Stepping Window, i is the step number | $T_1(i+1) = T_1(i) + \delta T$ $T_2(i+1) = T_2(i) + \delta T$ | const | $\Delta T$ |
| Sliding Window, i is the step number | $T_1(i+1) = T_1(i) + \delta T$ $T_2(i+1) = T_2(i) + \delta T$ | const | $<\Delta T$ |
| Adaptive Window | $T_1(1) = T_{min}$ $T_1(2) = T_2(1)$ $T_1(3) = T_2(2)$ $T_2(1) = T_1(1) + \Delta T(1)$ $T_2(2) = T_2(1) + \Delta T(2)$ $T_2(3) = T_{max}$ | $\Delta T(1)$ = large $\Delta T(2)$ = small $\Delta T(3)$ = large | — |
| Zooming Window | $T_1(1) = T_{min}$ $T_1(2) > T_1(1)$ $T_1(1) = T_{max}$ $T_1(2) = T_1(2) + \Delta T(2)$ | $\Delta T(1) = T_{max} - T_{min}$ $\Delta T(2)$ = small | — |
| Zooming Window with fixed $T_1$ | $T_1(i) = T_1(1), i < n$ $T_1(n) = T_2(n - 1)$ | const | — |

$T_1$ and $T_2$ are the set temperatures of the first and second ends of the fixture, respectively; $\Delta T = T_{2-T1}$ is the breadth of the temperature window; $\delta T$ the shift in the temperature window between steps, and i is the step number between 0 and n.

For three dimensional equilibrium melting curves analysis, spectra collected as a function of temperature through the thermal melting transition are analyzed by one of several chemometric methods including principle component analysis or singular value decomposition. Singular value decomposition can be used to extract basis spectra, linear combinations of which describe each of the spectra in the temperature profile. The matrix of UV spectra A, is decomposed into a matrix U, of orthogonal basis spectra, a matrix S, in which all of the elements are zero except for the singular values which lie on the diagonal, and a matrix V of coefficients which relate the basis vectors of U to the data matrix A; such that, $A=USV^T$. Examination of the auto-correlation functions of the basis spectra (columns of U) and the coefficient vectors (columns of V) permits one to determine the minimum number of component spectra required to describe the data within the random noise in the spectra. This provides experimental confirmation of one of the primary assumptions of the van't Hoff model; i.e., there are no thermodynamically significant intermediate states. The coefficient vectors, which represent the temperature-induced variation in the absorbance signal integrated over the entire spectral range, can be used to construct melting curves. This provides a melting curve with enhanced signal to noise relative to single wavelength curves. Thermodynamic analysis then proceeds as described in the art.

Alternate Applications of the Present Invention

The temperature gradient holding fixture as described above can be advantageously used for the investigation of layers of cells. Tissue samples or cultured cells may be placed or grown on the temperature gradient holding plate. Fluorescence due to indigenous or exogenous fluorophores, or other optical observables, may be observed as a function of position and therefore temperature. For example, the invention can be used for studying temperature dependence of chlorophyll fluorescence in plant cells.

The holding plate as described above can consist of the cover material that interacts with solution. Such interaction may be in a form of binding or a chemical reaction. Using temperature gradient fixture of the present invention, kinetic properties of this interaction such as a rate of chemical reaction can be investigated as function of temperature. An appropriate indicator (such as changing fluorescence or color for example) can be used to study this reaction.

The time dependence of chemical reactions may be investigated using the temperature gradient holding fixture of the invention to measure reaction rates as a function of temperature. With the resultant rate information, various kinetic and thermodynamic parameters can be determined including the optimum reaction temperature and the activation energy. Investigated reactions may include reactions catalyzed by enzymes. This is especially attractive since conventional methods would require a series of experiments conducted at different temperatures.

The temperature gradient holding fixture can also be used for investigation of physiological properties of the object. For example, the induction of chlorophyll fluorescence can be used to study photosynthesis. The temperature dependence of this value gives the optimum temperature and the activation (inhibition) rate of algae, phytoplankton or other cellular object.

Although the invention herein has been described with respect to particular embodiments, it is understood that these embodiments are merely illustrative of the principles and applications of the present invention. One possibility to use the method and device of the invention is to study temperature-dependent properties of a sample which are not optically observed. Various mechanical, electrical, and structural properties can be studied that way. For example, the temperature gradient fixture can allow studying the stiffness or elasticity of an elongated sample at various points along the fixture corresponding with different sample temperatures. Mechanical interrogation of the sample can be done by probing the sample at various locations along the fixture. Similar study may be done to evaluate the changing electrical conductivity of a sample as a function of temperature. It is therefore to be understood that numerous modifications may be made to the illustrative embodiments and that other arrangements may be devised without departing from the spirit and scope of the present invention as defined by the appended claims.

What is claimed is:

1. An apparatus for measuring a temperature-dependent property of a sample comprising:
    a first holding fixture to contain said sample, said holding fixture adapted to be thermally coupled to said sample, said holding fixture defining a first temperature point and a second temperature point,
    a temperature control system adapted to bring a temperature of said first temperature point to and maintain it at a predetermined first temperature level, said temperature control system further adapted to bring independently and at the same time a temperature of said second temperature point to and maintain it at a predetermined second temperature level, whereby defining the difference between said first and said second temperature levels as a temperature gradient between said first temperature point and second temperature point of said holding fixture, and
    an interrogation system adapted to interrogate said sample at a point of measurement and obtain said temperature-dependent property, said point of measurement having a known geometrical position relative to said first temperature point and said second temperature point of said holding fixture,
    whereby the temperature of said sample at said point of measurement is defined by said temperature gradient and said known geometrical position of said point of measurement relative to said first temperature point and said second temperature point of said holding fixture.

2. The apparatus as in claim 1, wherein said holding fixture has an internal cavity with a first end and a second end, said first temperature point located at said first end, said second temperature point located at said second end.

3. The apparatus as in claim 2, wherein said holding fixture comprising at least two parts forming together said internal cavity, said parts being dismountable to allow access inside said internal cavity.

4. The apparatus as in claim 2, wherein said holding fixture is covered with a non-reactive coating, said coating is selected from a group consisting of Parylene, anodized aluminum, gold, silver, a surface-bound polymer, and a self assembled monolayer.

5. The apparatus as in claim 2, wherein said holding fixture containing at least one optically transparent window and a minor placed opposite said window, said interrogation system including a bifurcated optical fiber.

6. The apparatus as in claim 1, wherein said holding fixture is made of metal, said metal is selected from a group consisting of gold, silver, copper, and aluminum.

7. The apparatus as in claim 1, wherein said holding fixture comprising a plate, adapted to be thermally coupled to said sample.

8. The apparatus as in claim 7, wherein said plate is smooth.

9. The apparatus as in claim 7, wherein said plate contains at least one channel adapted to accept said sample, said channel oriented along said temperature gradient between said first temperature point and said second temperature point.

10. The apparatus as in claim 9, wherein said plate contains a plurality of parallel channels adapted to accept one or more of said samples, said channels oriented along said temperature gradient between said first temperature point and said second temperature point.

11. The apparatus as in claim 7, wherein said plate is at least partially covered by a material interacting with said sample.

12. The apparatus as in claim 11, wherein said material is applied with a predetermined gradient of concentrations at various locations on said plate.

13. The apparatus as in claim 7, wherein said plate is covered with a self-adhesive disposable film.

14. The apparatus as in claim 13, wherein said film including optically observable labels.

15. A method for measuring a temperature-dependent property of a sample comprising the steps of:
   a) providing a holding fixture containing said sample, said holding fixture defining a first temperature point and a second temperature point,
   b) selecting the values of said first temperature and said second temperature;
   c) bringing a temperature at said first and said second temperature points respectively to said selected first and said second temperature values at the same time by heating or cooling said holding fixture at said first and said second temperature points,
   d) interrogating said sample to measure said temperature-dependent property of said sample at a point of measurement, said point of measurement having a known geometrical position relative to said first temperature point and said second temperature point of said holding fixture,
   e) determining a temperature of said sample at said point of measurement based on said first temperature, said second temperature and said known geometrical position of said point of measurement relative to said first temperature point and said second temperature point, and
   f) correlating said temperature-dependent property of said sample as measured in step (e) with the temperature of said sample as determined in step (e) for every point of measurement to elucidate a relationship between said property and said temperature for said sample.

16. The method as in claim 15, wherein said step (d) further including illumination from a first direction and Raman spectroscopy interrogation from a second direction.

17. The method as in claim 16, wherein said first direction is perpendicular to said second direction.

18. The method as in claim 15, wherein said step (d) including interrogation using total internal reflection fluorescence.

19. The method as in claim 15, wherein said temperature dependent property is a rate of chemical reaction, whereby said reaction rate as a function of temperature is obtained for said sample.

20. The method as in claim 19, wherein said reaction is catalyzed by at least one enzyme.

* * * * *